(12) United States Patent
Ishii

(10) Patent No.: US 8,693,746 B2
(45) Date of Patent: Apr. 8, 2014

(54) TECHNIQUE FOR DETECTING NEURODEGENERATIVE DISORDERS

(75) Inventor: Kazunari Ishii, Hyogo (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 435 days.

(21) Appl. No.: 13/056,614

(22) PCT Filed: Jul. 28, 2008

(86) PCT No.: PCT/JP2008/063502
§ 371 (c)(1),
(2), (4) Date: Apr. 12, 2011

(87) PCT Pub. No.: WO2010/013300
PCT Pub. Date: Feb. 4, 2010

(65) Prior Publication Data
US 2011/0188719 A1   Aug. 4, 2011

(51) Int. Cl.
*G06K 9/00* (2006.01)

(52) U.S. Cl.
USPC .......................................... 382/128; 382/131

(58) Field of Classification Search
USPC ........... 382/100, 128–132; 128/920; 600/101, 600/109, 112, 114, 117–118, 139, 145, 173, 600/420, 424, 427, 434, 415
See application file for complete search history.

(56) References Cited

U.S. PATENT DOCUMENTS

| | | | |
|---|---|---|---|
| 5,262,945 A * | 11/1993 | DeCarli et al. | 600/410 |
| 5,632,276 A | 5/1997 | Eidelberg et al. | |
| 5,873,823 A | 2/1999 | Eidelberg et al. | |
| 7,742,763 B2 * | 6/2010 | Jiang | 455/433 |
| 8,165,362 B2 * | 4/2012 | Ishii et al. | 382/128 |
| 2005/0215889 A1 * | 9/2005 | Patterson, II | 600/436 |
| 2006/0276462 A1 * | 12/2006 | Deadwyler et al. | 514/229.5 |
| 2009/0290765 A1 * | 11/2009 | Ishii et al. | 382/128 |
| 2009/0290772 A1 * | 11/2009 | Avinash et al. | 382/130 |
| 2011/0103656 A1 * | 5/2011 | Iordanescu et al. | 382/128 |
| 2011/0129131 A1 * | 6/2011 | Avinash et al. | 382/128 |
| 2011/0160543 A1 * | 6/2011 | Parsey et al. | 600/300 |
| 2011/0194741 A1 * | 8/2011 | Ekin et al. | 382/128 |

FOREIGN PATENT DOCUMENTS

| | | |
|---|---|---|
| JP | 2005-237441 | 9/2005 |
| JP | 2006-051170 | 2/2006 |
| JP | 2006-204641 | 8/2006 |
| JP | 2010-512784 | 4/2010 |
| WO | WO 96/22729 | 8/1996 |
| WO | WO 2007/063656 | 6/2007 |

OTHER PUBLICATIONS

Friston et al., "Statistical Parametric Maps in Functional Imaging: A General Linear Approach", Human Brain Mapping, Apr. 7, 1995, 2, 189-210.

(Continued)

*Primary Examiner* — Hadi Akhavannik
*Assistant Examiner* — Mehdi Rashidian
(74) *Attorney, Agent, or Firm* — Baker & Hostetler LLP

(57) ABSTRACT

In one embodiment of the present invention, a significance test of pixel values is performed between a region where functions could be deteriorated in a disease-specific manner and a region where functions could be preserved even in cases of diseases using brain functional images. Then, the mean pixel value of the functionally preserved site is significantly greater than the mean pixel value of the functionally deteriorated site according to the significance test is determined as an a image including a neurodegenerative disorder. According to this embodiment, it becomes possible to objectively detect images of neurodegenerative disorders without using a database for healthy subjects.

20 Claims, 10 Drawing Sheets

(56) References Cited

OTHER PUBLICATIONS

Herholz et al., "Discrimination between Alzheimer Dementia and Controls by Automated Analysis of Multicenter FDG PET", NeuroImage, Sep. 2002, 17(1), 302-316.

PCT Application No. PCT/JP2008/063502, International Search Report, Filing Date: Jul. 7, 2008, Mailing Date: Sep. 22, 2008, 3 pages.

Ishii, "Clinical Application of Positron Emission Tomography for Diagnosis of Dementia", Annals of Nuclear Medicine, Nov. 11, 2002, 16(8), 515-252.

Minoshima et al., "Anatomic Standardization: Linear Scaling and Nonlinear Warping of Functional Brain Images", The Journal of Nuclear Medicine, Sep. 1994, 35(9), 1528-1537.

European Patent Application No. EP 08791737: Extended European Search Report dated Feb. 28, 2012, 6 pages.

Minoshima, et al., "A Diagnostic Approach in Alzheimer's Disease Using Three-Dimensional Stereotactic Surface Projections of Fluorine-18-FDG PET", The Journal of Nuclear Medicine, Jul. 1995, 36(7), 1238-1248.

Foster et al, "FDG-PET improves accuracy in distinguishing frontotemporal dementia and Alzheimer's disease", Brain, Oct. 2007, 130(Pt 10), 2616-2635.

Canadian Patent Application No. 2,271,657: Office Action dated Jun. 22, 2012, 3 pages.

* cited by examiner (a) Parietal lobe (b) Temporal lobe (c) Sensorimotor area (d) Frontal lobe (e) Occipital lobe (f) Posterior cingulate gyrus (g) Anterior cingulate gyrus (a) Functionally deteriorated site (b) Functionally preserved site

TECHNIQUE FOR DETECTING NEURODEGENERATIVE DISORDERS

CROSS-REFERENCE TO RELATED APPLICATION

This application is the National Stage of International Application No. PCT/JP2008/063502, filed Jul. 28, 2008, titled TECHNIQUE FOR DETECTING CRANIAL NERVE DISEASE as amended during the International Phase, the disclosure of which is incorporated herein by reference in its entirety.

FIELD OF THE INVENTION

The present invention relates to a technique for detecting neurodegenerative disorders such as Alzheimer's disease and Lewy body dementia, and preferred embodiments include a detection program for images including a neurodegenerative disorder, a method for detecting images including said neurodegenerative disorder using a computer, and an apparatus for detecting images including a neurodegenerative disorder.

BACKGROUND OF THE INVENTION

As a result of increases in the elderly population, it is expected that the number of patients with neurodegenerative disorders involving forms of dementia such as Alzheimer's disease will increase. Because these diseases progress with age and affect both the patient and their living environment, it is important to diagnose such cases at an early stage.

Such neurodegenerative disorders involving dementia are diagnosed by applying the results of, for example, neuropsychological tests, including the well-known Mini Mental Status Examination (hereinafter referred to as "MMSE"), as well as interviews and clinical findings, etc. to diagnostic criteria such as DSM-III-R or ICD-10. These diagnoses do not necessarily have high specificity. So these diagnoses are combined with diagnostic imaging such as CT, MRI, or SPECT in order to improve the diagnostic accuracy rate. However, even when diagnostic imaging such as CT, MRI, or SPECT is involved, because the diagnostic accuracy of diagnostic imaging depends on the level of proficiency and the subjectivity of the radiography interpreter, there is a problem in that the results vary between facilities and examiners. Accordingly, there has been a desire for techniques allowing for neurodegenerative disorders to be detected in a more objective manner.

Recent studies have shown that in cases of neurodegenerative disorders involving dementia, brain functions such as cerebral blood flow and glucose metabolic rate become partially deteriorated (See below Non-patent Document 1). Using this knowledge, The below Non-patent Document 2 discloses a method of using positron-emission tomography (hereinafter referred to as "PET") images obtained by administering the glucose metabolism tracer 2-[18F]fluoro-2-deoxy-D-glucose (hereinafter referred to as "FDG") to conduct comparisons with a healthy group, calculate the t-values of the pixel values for each pixel, and discriminate between Alzheimer's disease patients and healthy subjects.

Further, International Publication No. 2007/063656 discloses methods for objectively detecting images based on neurodegenerative disorders at an early stage by calculating t-values or z-scores based on comparisons with a healthy subject database for pixels within a preset region of interest in a subject image, and defining a fixed threshold value for the obtained t-values or z-scores (Patent Document 1).

KNOWN PRIOR ART DOCUMENTS

[Non-patent Document 1] Kazunari Ishii, "Clinical application of positron emission tomography for diagnosis of dementia", Annals. of Nuclear Medicine, 2002, 16(8), p. 515-525

[Non-patent Document 2] K. Herholz et al., "Discrimination between Alzheimer dementia and controls by automated analysis of multicenter FDG PET", NeuroImage, 2002, 17, p. 302-316

[Patent Document 1] International Publication No. 2007/063656

DISCLOSURE OF THE INVENTION

Problems to be Solved by the Invention

As described above, for neurodegenerative disorders, there is a need for techniques that are capable of objectively detecting early-stage lesions. As disclosed by Herholz, etc., by measuring local deteriorations in brain functions such as glucose metabolism, etc., it is possible to detect Alzheimer's disease and other neurodegenerative disorders. However, in order to detect Alzheimer's disease and other neurodegenerative disorders using diagnostic imaging, it is necessary to define conditions for discriminating the neurodegenerative disorders from other conditions to perform detection. Moreover, because this method is a method based on comparisons with healthy subject data, for implementation, it is necessary to prepare a database for healthy subjects.

According to the technique disclosed in International Publication No. 2007/063656, it is possible to discriminate images of Alzheimer's disease and other neurodegenerative disorders from other conditions to perform an objective determination. However, as with the above method disclosed by Herholz, etc., because this method is also a method based on comparisons with healthy subject data, it is necessary to prepare a database for healthy subjects to practice the technique.

However, most subjects undergoing imaging tests in hospitals, etc., generally present with some kind of lesions, and therefore, it is not easy to create an image database of healthy subjects. Consequently, it is preferable if there is no need to use a database for healthy subjects for distinguishing and determining images of neurodegenerative disorders patients from images of healthy subjects objectively and accurately, but such technique has not been found yet.

The present invention has been devised based on the above considerations, and the objective is to provide a technique for detecting neurodegenerative disorders such as Alzheimer's disease and Lewy body dementia, etc. based only on brain functional images of the subject and without using a database for healthy subjects.

Solutions to the Problems

As a result of numerous studies, the present inventors discovered that in a brain functional image, there is a disease-specific region where the probability of functional deterioration is high (hereinafter sometimes referred to as "functionally deteriorated site") as well as a disease-specific region where the probability of functional preservation is high even in cases of diseases (hereinafter sometimes referred to as "functionally preserved site"), and that it is possible to objectively determine images in which a neurodegenerative disorder is believed to exist without using a healthy subject database by comparing the respective pixel values of the functionally deteriorated site and the functionally preserved site.

Based on this discovery, it becomes possible to determine a neurodegenerative disorder using the same brain functional images of the same subject. In other words, it becomes possible to determine images containing a neurodegenerative disorder using only images derived from the subject, without the need to prepare a database for healthy subjects.

[Demonstration 1: Example of Determining Images of Alzheimer's Disease Patients]

As one example for demonstrating that neurodegenerative disorders can be detected using the above technique, images derived from Alzheimer's disease patients and images derived from healthy subjects were used to obtain the sensitivity, specificity, and diagnostic accuracy rate of the technique according to the present invention.

(Setting of Regions of Interest)

To define the regions of interest, $^{123}$I-IMP-administered brain SPECT images of 20 Alzheimer's disease patients (mean age: 73.6±4.6 years old) and 15 healthy subjects (mean age: 60.5±7.1 years old) were used (hereinafter, the groups are respectively referred to as the "disease group" and the "healthy group").

For each image, software called as iNEUROSTAT (produced by Nihon Medi-Physics Co., Ltd.) was used to perform anatomic standardization. Then the pixel values of each image were subtracted by the respective mean values of all pixel values in each image to normalize the pixel values (hereinafter collectively referred to as "normalized images").

Using these images, an inter-group comparison was conducted between the disease group and the healthy group, and z-scores representing decreases in pixel value were obtained for each pixel. The obtained z-scores were put on corresponding pixels. And clusters representing regions with decreased pixel values were extracted by using the threshold value of 3. From the obtained clusters, the largest cluster was selected and defined as functionally deteriorated region 1. Similarly, z-scores representing increases were obtained, and a threshold value of 3 was employed to extract clusters representing regions with increased pixel values. From the obtained clusters, the largest cluster was selected and defined as functionally preserved region 1.

Separately, for brain template stored in the iNEUROSTAT program (FIG. 5), segments indicating functionally deteriorated regions and segments indicating functionally preserved regions were selected by comparing the template with the normalized images. Each selected segment was compared with both said functionally deteriorated region 1 and said functionally preserved region 1. And regions with substantive commonality were extracted and used as region-of-interest data corresponding to the functionally deteriorated site and the functionally preserved site, respectively (FIG. 9).

(Evaluation of Sensitivity, Specificity, and Diagnostic Accuracy Rate of Image Detection for Alzheimer's Disease Patients)

To evaluate the sensitivity, specificity, and diagnostic accuracy rate, the $^{123}$I-IMP-administered brain SPECT images of 17 Alzheimer's disease patients (mean age: 60.1±8.2 years old) and 17 healthy subjects (mean age: 61.1±7.3 years old) were used. For each image, the software iNEUROSTAT was applied for anatomic standardization, and the region-of-interest data obtained above were applied to define regions of interest for the functionally deteriorated site and the functionally preserved site respectively. For each image, a t-test was performed between the functionally deteriorated site and the functionally preserved site for pixel values with a risk rate of 5%. Images in which the mean pixel value of the functionally preserved site was determined to be significantly greater than the mean pixel value of the functionally deteriorated site by the t-test were determined as images of Alzheimer's disease patients, and the other images were determined as healthy subject images. Based on these results, the sensitivity, specificity, and diagnostic accuracy rate were obtained using heretofore known techniques.

The sensitivity, specificity, and diagnostic accuracy rate were 82.4%, 88.2%, and 85.3%, respectively. Each shows high value. Based on the above results, it was confirmed that the technique according to the present invention can detect patient images derived from Alzheimer's disease objectively and with high accuracy.

[Demonstration 2: Example of Detection of Lewy Body Dementia]

As yet another example for demonstrating that neurodegenerative disorders can be detected using techniques according to the present invention, images derived from Lewy body dementia patients and images derived from healthy subjects were used to seek the sensitivity, specificity, and diagnostic accuracy rate of detection of the disease.

(Settings of Regions of Interest)

To define the regions of interest, $^{123}$I-IMP-administered brain SPECT images of 15 Lewy body dementia patients (mean age: 79.0±6.6 years old) were used.

For each image, the program iNEUROSTAT (produced by Nihon Medi-Physics Co., Ltd.) was used to perform anatomic standardization. These standardized images were compared with the brain template (FIG. 5) stored in the iNEUROSTAT software. Based on the comparison, the occipital lobe was selected as a segment indicating a functionally deteriorated site and used as region-of-interest data. Similarly, the sensorimotor area was selected as a segment indicating a functionally preserved site and used as region-of-interest data.

(Evaluation of Sensitivity, Specificity, and Diagnostic Accuracy Rate of Image Detection for Lewy Body Dementia Patients)

To evaluate the sensitivity, specificity, and diagnostic accuracy rate, the $^{123}$I-IMP-administered brain SPECT images of 15 Lewy body dementia patients (mean age: 79.0±6.6 years old) and 15 healthy subjects (mean age: 60.5±7.1 years old) were used (hereinafter, the groups are respectively referred to as the "DLB disease group" and the "healthy group"). For each image, the iNEUROSTAT software was used for anatomic standardization, and the region-of-interest data obtained above were applied to define regions of interest in the functionally deteriorated site and the functionally preserved site respectively. For each image, a t-test was performed between the functionally deteriorated site and the functionally preserved site for pixel values with a risk rate of 5%. Images in which the mean pixel value of the functionally preserved site was determined to be significantly greater than the mean pixel value of the functionally deteriorated site by the t-test were determined as images of Lewy body dementia, and the other images were determined as images of healthy subject. Based on these results, the sensitivity, specificity, and diagnostic accuracy rate were obtained using heretofore known techniques.

The sensitivity, specificity, and diagnostic accuracy rate were 73.3%, 86.7%, and 80.0%, respectively. Each value is high. Based on the above results, it was confirmed that the technique according to the present invention enables to detect Lewy body dementia objectively and with high accuracy.

As can be understood from the above two examples, some neurodegenerative disorders show a region where the possibility of functional deterioration is high and a region where the possibility of functional preservation is high, in brain functional images. And in cases of such diseases, it is possible to detect the disease by comparing brain functional images between these regions. The Demonstrations introduced in the present specification are limited to Alzheimer's disease and Lewy body dementia, but it is clear that the present invention can be applied to various neurodegenerative disorders presenting with a functionally deteriorated site and a functionally preserved site in brain functional images. Examples of diseases with a very high potential for applicability include Alzheimer's disease, Lewy body dementia, frontotemporal dementia, and progressive supranuclear palsy, etc.

One important aspect is that, in order to identify a disease-specific functionally deteriorated site and a functionally preserved site, although there are cases in which it is preferable to have healthy subject data, once those sites are identified, such healthy subject data become unnecessary, and it becomes possible to detect a disease using only images derived from a subject. Operations to identify these sites do not necessarily have to be performed at a general hospital and may be performed at a specialized research institute. Once a functionally deteriorated site and a functionally preserved site specific to a certain disease are identified, and if that data becomes available for use, owners of a device according to the present invention should immediately be able to begin operations to determine related diseases by using the data, without having to construct a healthy subject database as before.

In this way, the present invention makes the operations required for determining an existence of neurodegenerative disorders extremely easy compared to before, and can contribute great advantages in the fields of medical service and image analysis programs.

In the present specification, data on disease-specific functionally deteriorated sites and functionally preserved sites may be referred to as region-of-interest data. As can be seen in the above explanations, the region-of-interest data are used for extracting regions for performing inter-region comparisons. In cases of Alzheimer's disease, the functionally deteriorated site and the functionally preserved site can be defined as the parietal lobe and the sensorimotor area, respectively. In cases of Lewy body dementia, the functionally deteriorated site and the functionally preserved site can be defined as the occipital lobe and the sensorimotor area, respectively. As described above, once region-of-interest data are obtained in one facility, the need for other facilities to perform the same experiments is greatly reduced and that data can be also be used at other facilities.

Region-of-interest data can be obtained through various techniques. For example, such data can be obtained based on the results of an inter-group comparison between brain functional images derived from multiple subjects affected by a neurodegenerative disorder (hereinafter referred to as the "disease group") and brain functional images derived from multiple healthy subjects (hereinafter referred to as the "healthy group"). By using this technique, it is possible to define regions of interest in sites that statistically show functional deterioration and sites that statistically show functional preservation in cases of the subject disease. For the inter-group comparison, any heretofore known technique, such as techniques described in the literature (International Publication No. 2007/063656), for example, can be used. Here, It is preferable to normalize each of the images included in the disease group and the healthy subject group using the mean of all pixel values in each image, and the use them. By performing normalization operations, the pixel values of the functionally preserved site in the disease group become relatively higher, making extraction based on the inter-group comparison easier.

It is possible to obtain region-of-interest data from a different way, which uses only brain functional images derived from patients affected by a neurodegenerative disorder. Specifically, it is possible to use a technique of defining a threshold value for the pixel values in a brain functional image to extract a functionally deteriorated site and a functionally preserved site for use as region-of-interest data.

It is also possible to obtain region-of-interest data from further different way, which uses a predetermined template for a standard brain. For example, it is possible to select segments corresponding to a disease-specific functionally deteriorated site and functionally preserved site from the various region data that have been defined in the Talairach brain atlas or other brain atlases, etc., for use as region-of-interest data.

Although the techniques for defining region-of-interest data exemplified above may each be used independently, it is also possible to use two or more techniques in combination. For example, it is possible to use region-of-interest data defined by two different techniques to perform region extraction for each, and define regions commonly extracted through both techniques as region-of-interest data. By using region-of-interest data obtained by combining two or more techniques, it can be expected that the accuracy of disease detection will be further improved.

In order for the region-of-interest data to have versatility, it is preferable if the region-of-interest data presents a functionally deteriorated site and a functionally preserved site in an anatomically standardized brain image (standard brain). Consequently, in a preferred embodiment, analysis is conducted after the brain functional images of a subject undergoing disease detection also undergo anatomic standardization. Alternatively, the region-of-interest data may be modified to match the brain functional images of the subject for use in analysis. For anatomic standardization, a heretofore known technique described in the literature (Minoshima S. et al., J. Nucl. Med., 1994, 35, p. 1528-37, or Friston K. J. et al., Human Brain Mapping, 1995, 2, p. 189-210), for example, may be used.

In the present specification, regions for actually comparing image data to perform disease determination may be referred to as regions of interest. The regions of interest may be regions that are automatically extracted using the above region-of-interest data, but further adjustments may be made either automatically or manually.

According to one embodiment, comparisons between regions of interest may be performed by comparing the pixel values of image data contained in each region of interest. Generally, blood flow and glucose metabolism of a subject presenting with a disease decrease depending on regions. Such regions appear darker than other regions in brain functional images obtained through SPECT or PET, etc. Consequently, if at least a certain number of pixel values of the regions of interest of a functionally deteriorated site are smaller than the pixel values of the regions of interest of a functionally preserved site, it is possible to infer the presence of a disease. However, because there may be errors in determination due to noise, etc. when performing a simple comparison of mean values, etc., it is preferable to perform a comparison using a significance test such as a t-test, etc. In such configuration, it is preferable to use a configuration for determining whether the mean pixel value of the regions of interest of the functionally preserved site is significantly greater than the mean pixel value of the regions of interest of the functionally deteriorated site, rather than using a configuration for simply determining the presence or absence of a significant difference. By using such a configuration, the rate of errors in judgment can be roughly halved.

Embodiments of the present invention include neurodegenerative disorders image detecting apparatuses such as the following. This device comprises a region-of-interest defining section that defines regions of interest in a functionally deteriorated site where functions could be specifically deteriorated in a neurodegenerative disorder to be detected, and a functionally preserved site where functions could be preserved even in said neurodegenerative disorder to be detected, respectively, in said brain functional image; and a disease-image determination section that is configured to conduct a significance test using pixel values within said regions of interest defined for each of said functionally deteriorated site and said functionally preserved site, and determine that said neurodegenerative disorder to be detected is present if the mean pixel value of said regions of interest in said functionally preserved site is significantly greater than the mean pixel value of said regions of interest in said functionally deteriorated site.

Other embodiments of the present invention include computer programs such as the following. This program is capable of handling image data composing brain functional images and is a computer program for operating a computer equipped with a storage means and a CPU, and when the program is executed by said CPU, the program operates the computer as: a first memory means for storing image data corresponding to a first region of a brain functional image; a second memory means for storing image data corresponding to a second region different from said first region in said brain functional image; and a neurodegenerative disorders detection means that determines neurodegenerative disorders based on a comparison of the image data stored in said first memory means and the image data stored in said second memory means.

In a preferred embodiment, the above first and second memory means may be memory that is logically formed on a physical medium by the program. The program may be configured so that in either one of the first and second memory means, image data of a site where functions may specifically deteriorate in cases of the neurodegenerative disorders in a disease to be detected are saved, and in the other means, image data of a site where functions may be preserved even in cases of the neurodegenerative disorders are saved. In other words, in a preferred embodiment, the above first and second regions are regions of interest that have been respectively defined for the above functionally deteriorated site and the functionally preserved site.

Other embodiments of the present invention include methods for detecting neurodegenerative disorders images such as the following. This method comprises: a step for defining regions of interest in a functionally deteriorated site where functions could be specifically deteriorated in a neurodegenerative disorder to be detected, and a functionally preserved site where functions could be preserved even in said neurodegenerative disorder to be detected, respectively, in said brain functional image; and a disease-image determining step for performing a significance test using pixel values of regions of interest defined in each of said functionally deteriorated site and said functionally preserved site, and determining that said neurodegenerative disorder to be detected exists if the mean pixel value of said regions of interest in said functionally preserved site is significantly greater than the mean pixel value of said regions of interest in said functionally deteriorated site.

The various embodiments of the present invention include those that perform anatomic standardization of the brain functional images. In this way, regions of interest can be defined for standardized brain functional images. Conversely, it is also possible to use a technique of using inverse transformation to transform region-of-interest data defined with a standard brain into the form of the brain functional images of the subject, and superimposing the transformed region-of-interest data on the brain functional images of the subject to define the regions of interest on the brain functional images of the individual subject.

As described above, it is preferable to configure the data to be automatically called in response to information such as disease name, etc, because the region-of-interest data are disease-specific.

Several preferred embodiments of the present invention are specified in the attached Claims. However, embodiments of the present invention are not limited to those explicitly described in the Claims or the Description and Drawings, and the present invention may take on various configurations without deviating from the sprits of the present invention. The present invention includes in its scope any new and beneficial configurations that may be suggested in these documents, regardless of whether such configurations are explicitly disclosed in the Claims or the Description and Drawings of the present application.

BEST MODE FOR CARRYING OUT THE INVENTION

Embodiments of techniques according to the present invention for detecting images containing a neurodegenerative disorder will be described in detail with reference to the drawings. It should be noted that the example described below only provides a description of an example believed to be the most optimal, and the embodiments of the present invention is not limited in any way by these descriptions.

FIG. 1A is a diagram showing the configuration of an optimal mode for a neurodegenerative disorders image detecting apparatus 20 according to the present invention. FIG. 2 is a diagram showing the operations of the optimal mode of the neurodegenerative disorders image detecting apparatus 20 according to the present invention. The neurodegenerative disorders image detecting apparatus 20 according to the present invention may be configured as a computer into which a neurodegenerative disorder image detection program 100 (described below) has been read. As shown in FIG. 1A, the neurodegenerative disorders image detecting apparatus 20 according to the present invention functionally comprises: an image acquirer 22 that acquires a brain functional image from a brain function imaging apparatus 10 such as a SPECT apparatus, etc.; an image standardization section 24 that is configured to perform anatomic standardization of the acquired brain functional image; a region-of-interest defining section (described as "ROI defining section" in FIG. 1A) 26 that defines regions of interest in the standardized brain functional image; a disease-image determination section 28 that determines whether said brain functional image corresponds to an image of the disease to be detected; and an output section 30 that outputs the detection results.

FIG. 1B is an explanatory diagram of the hardware configuration of the image detecting apparatus 20. As shown in FIG. 1B, the image detecting apparatus 20 comprises a CPU 40, a main memory 42, an auxiliary storage unit 44, and, preferably, a communication unit 46, etc. In other words, in terms of hardware, the image detecting apparatus 20 may have the same configuration as a general-purpose computer. In the auxiliary storage unit 44, which may be a hard disk, etc., a program for operating apparatus 20 as a neurodegenerative disorders image detecting apparatus is stored, and when this program is executed by the CPU 40, the functions required for detecting neurodegenerative disorders are provided. In other words, part or all of the functions of the image acquirer 22, the image standardization section 24, the ROI defining section 26, and the disease-image determination section 28, etc., are realized using software processing.

In a preferred mode, an auxiliary storage unit 50, a display 52, and user interfaces 54-58, etc. are connected to the image detecting apparatus 20 via external interfaces 48a-48e. The user interfaces 54-58 may be, for example, a touch panel 54, a keyboard 56, and a mouse 58, etc. The auxiliary storage unit 50 may be, for example, an optical disk drive such as a DVD-ROM drive, etc. According to one embodiment, the touch panel 54 is configured by being integrated in the display 52. In a preferred embodiment, the brain function imaging apparatus 10 is connected to the image detecting apparatus 20 via the communication unit 46, and it is possible to download images captured with the brain function imaging apparatus 10 into the auxiliary storage unit 44 via a network.

The embodiment will now be described mainly with reference to FIG. 1A. Various devices that are capable of acquiring brain functional images may be used as the cranial functional imaging apparatus 10. Specific examples include a SPECT apparatus, a PET device, an MRI device, or a CT device. The brain function imaging apparatus 10 includes an imager 12 and an image reconstructor 14. The imager 12 acquires the brain functional image data of a subject. The image reconstructor 14 performs image reconstruction processes for the acquired brain functional image data to generate a brain functional image. Using the example of a SPECT apparatus, the imager 12 acquires projection data from a subject who has been administered radiopharmaceutical agents such as $^{99m}$Tc HMPAO and $^{123}$I IMP. These projection data correspond to the brain functional image data of the present embodiment. The image reconstructor 14 performs the necessary reconstruction processes for the acquired projection data and generates a series of tomographic images. This series of tomographic images corresponds to the brain functional images of the present embodiment. The image reconstruction can be performed using a heretofore known technique.

The image acquirer 22 acquires the brain functional image generated in the image reconstructor 14 (step S1). The brain functional image is saved in a computer-readable data format such as, for example, DICOM. In order to transfer the saved brain functional image data to the image detecting apparatus 20, the data may be stored in a storage medium such as a DVD, etc. in the brain function imaging apparatus 10, and such disk may be inserted into a reading device (the auxiliary storage unit 50). Preferably, the data may be directly transferred to the auxiliary storage unit 44 via the communication unit 46 as computer data signals conveyed on carrier waves. As described above, the auxiliary storage unit 44 may be a hard disk or a unit of flash memory, etc. In a preferred embodiment, the image acquirer 22 reads brain functional image data stored in the auxiliary storage unit 44 or the auxiliary storage unit 50 and stores the data in a logical memory region formed on the main memory 42 or the auxiliary storage unit 44 using software. The stored data are provided for processing at the next processing block (the image standardization section 24).

The image standardization section 24 performs an anatomic standardization process on the brain functional image acquired by the image acquirer 22, and transforms the brain functional image into a standard brain (step S2). This anatomic standardization process may be performed using a heretofore known technique described in the technique (Minoshima S. et al., J. Nucl. Med., 1994, 35, p. 1528-37, or Friston K. J. et al., Human Brain Mapping, 1995, 2, p. 189-210), for example. The transformed brain image data are stored in a logical memory region formed on the main memory 42 or the auxiliary storage unit 44 using software. In some embodiments, the transformed brain image data may be displayed on the display 52.

The region-of-interest defining section 26 defines regions of interest in a site where functional deterioration may occur in cases of the disease to be detected (functionally deteriorated site), and a site with a high possibility of functional preservation (functionally preserved site), respectively, in the brain functional image transformed to the standard brain (step S5). In a preferred mode, the region-of-interest defining section 26 is linked to both a disease-information input section 32 and a region-of-interest database (described as "ROI data" in FIG. 1A) 34 stored in the auxiliary storage unit 44 or 55, etc.

The disease-information input section 32 is capable of receiving inputs from at least one of the user interfaces 54-58, and receives inputs of information on the disease to be detected, most typically the disease name (step S3). As long as the disease information is information that can be used for selecting region-of-interest data from said database, there are no particular limitations to the disease information. Typically, the information may be the common name of the neurodegenerative disorders, but abbreviations or typical symptoms, etc. may be used. For the input of disease information, it is also possible to combine heretofore known techniques related to menu selection, such as displaying disease information in a pull-down menu and making the subject disease selectable, etc.

In a region-of-interest database 34, data on sites that should be subject to examination for each neurodegenerative disorders—in other words, data on sites where functions may deteriorate in cases of the disease (functionally deteriorated site) and sites with a high possibility of functional preservation even in cases of the disease (functionally preserved site) (i.e., region-of-interest data)—are stored and associated with disease information. Based on the input disease information, the region-of-interest defining section 26 reads the region-of-interest data corresponding to the disease to be detected (step S4), and defines regions corresponding to the region-of-interest data in said brain functional image that has been transformed to the standard brain as regions of interest (step S5). For the region-of-interest data, It is possible to employ data formed using various techniques may be used. Techniques for forming region-of-interest data will be described later.

In some embodiments, the defining of regions of interest may be configured to be performed manually instead of through automatic defining using region-of-interest data. It may also be possible for the operator to automatically or manually adjust automatically define regions of interest. For example, a configuration may be provided in which the operator uses a touch panel 54 or a mouse 56, etc. to select desired regions on a brain image displayed on the display 52 to determine regions of interest. Further, a configuration may be provided in which a brain atlas is overlapped and displayed over a brain functional image of a subject transformed to a standard brain, and desired regions can be selected using the user interfaces 54-58.

The region-of-interest defining section 26 stores region-of-interest data defined respectively for the functionally deteriorated site and the functionally preserved site in different logical memories (logical memory regions formed on the main memory 42 and the auxiliary storage unit 44 using software). The stored image data are provided for the following processes.

The disease-image determination section 28 performs a process for detecting images containing a neurodegenerative disorder (step S6). FIG. 3 is a flow chart showing processes in the disease-image detection process. The disease-image determination section 28 reads the data that was stored in each of the logical memories in step S5 and conducts a significance test of the pixel values between the pixels in the functionally deteriorated site and the pixels in the functionally preserved site (step S11). The significance test may be performed using a heretofore known technique. In an optimal mode, a t-test may be used for the significance test. As a result of this significance test, if it is determined that the mean pixel value of the functionally preserved site is significantly greater than the mean pixel value of the functionally deteriorated site ("Yes" in step S12), the image is determined to be an image in which the neurodegenerative disorders to be detected may exist (step S13). On the other hand, if the mean pixel value of the functionally preserved site is not significantly greater than the mean pixel value of the functionally deteriorated site ("No" in step S12), the image is not determined to be an image containing the neurodegenerative disorders to be detected (step S14). The disease-image determination section 28 stores the necessary data, such as the results of determinations, in a logical memory, and the disease-image detection process (step S6) is completed.

The output section 30 outputs the results of the detection process performed by the disease-image determination section 28 to the display 52 via a display interface 48b (step S7). Outputs may also be made to other output devices, such as a printer or a sound generator, etc. The format of the output does not necessarily have to be limited, and may be a format in which the t-value or the detection result (or both) is displayed on the image, or a format in which a color is allocated to distinguish the image from others if the mean pixel value of the functionally preserved site is determined to be significantly greater than the mean pixel value of the functionally deteriorated site.

As described above, it is possible to employ various types of data obtained by different techniques for the region-of-interest data to be stored in the region-of-interest database. Some examples of techniques for defining region-of-interest data will be explained below, which include a technique based on disease images, a technique using a template defined on a standard brain, and a technique based on an inter-group comparison between a disease group and a healthy subject group.

First, a case in which region-of-interest data are defined based on disease images will be described. In this example, first, an image derived from a patient affected by the neurodegenerative disorders to be detected (e.g., Alzheimer's disease) is acquired. For the disease image, it is preferable to use an image that has been preliminarily transformed to a standard brain. The disease image may also be obtained by averaging the pixel value of each pixel in images derived from multiple patients that have been transformed to a standard brain. Or it is possible to use representative examples exhibiting typical image patterns for each disease. Then, for the acquired disease image, the functionally deteriorated site and the functionally preserved site are both extracted using the threshold value technique. These site-data will be used as region-of-interest data. Examples of region-of-interest data extracted according to the present technique are shown in FIG. 4(a) and FIG. 4(b). FIG. 4(a) and FIG. 4(b) respectively show the functionally preserved site and the functionally deteriorated site in a case in which the disease to be detected is Alzheimer's disease. Each region of interest corresponding to the functionally deteriorated site and the functionally preserved site may be defined using the same disease image, but they may each be defined using different images.

Next, the technique of using a brain template defined on a standard brain will be described. In this technique, a brain template that has been anatomically defined on a standard brain is compared with a disease image, and regions (segments) corresponding to the functionally deteriorated site and the functionally preserved site are selected. FIG. 5(a)-(g) shows one example of a brain template. It is possible to compare this brain template to the image undergoing detection, select segments corresponding to the functionally deteriorated site and the functionally preserved site in the disease to be detected, and use these as region-of-interest data corresponding to the disease.

Next, the technique based on an inter-group comparison between a disease group and a healthy subject group will be described. In this technique, first, a plurality of disease images and a plurality of healthy subject images are acquired. Then, an anatomic standardization is performed for each acquired image, and then an inter-group comparison is performed for each pixel to obtain values that will act as indices of the amount of change in the pixel values, such as t-values or z-scores (hereinafter referred to as "index values"). The corresponding index values are displayed on each pixel on the standard brain, and using the threshold value technique, the functionally deteriorated site and the functionally preserved site are both extracted and used as region-of-interest data.

The above-mentioned techniques may be used independently, or may be used with two or more of them in combination. For example, regions of interest extracted through each of the above techniques may be displayed in overlapped manner, and the common areas may be extracted and may be used as region-of-interest data. By combining two or more techniques in such manner, it becomes possible to further improve the accuracy of detection of disease images.

Next, a neurodegenerative disorder detection program according to the present invention will be described. FIG. 6 is a diagram showing a configuration according to an optimal mode of the neurodegenerative disorders image detection program 100 according to the present invention, along with a storage medium 200.

In a preferred mode, the neurodegenerative disorders image detection program 100 according to the present invention comprises a main module 110 that controls the processes, an image-data acquisition module 120, an image standardization module 130, a disease-information input module 140, a region-of-interest defining module 150 (described as "ROI defining module" in FIG. 6), a disease-image detection module 160, and an output module 170.

In a preferred embodiment, the neurodegenerative disorders image detection program 100 is provided by being stored in the storage medium 200. Examples of the storage medium 200 include a flexible disk, a hard disk, a CD-ROM, a DVD, or a semiconductor memory, etc. By inserting the storage medium 200 that stores the neurodegenerative disorders image detection program 100 into a reading device (e.g., the auxiliary storage unit 50 of FIG. 1B) built into a computer, the neurodegenerative disorders image detection program 100 becomes available for access by the computer, and using this program 100, it becomes possible for the computer to operate as the neurodegenerative disorders detecting apparatus 20 described above. Of course, the program 100 may be installed and used in a high-speed memory unit (e.g., the auxiliary storage unit 44 of FIG. 1B), such as a hard disk, etc. The neurodegenerative disorders image detection program 100 according to the present invention may be provided via a network as computer data signals conveyed on carrier waves.

The image-data acquisition module 120 causes the computer to function as the image acquirer 22. The image standardization module 130 causes the computer to function as the image standardization section 24. The disease-information input module 140 causes the computer to function as the disease-information input section 32. The region-of-interest defining module 150 causes the computer to function as the region-of-interest defining section 26. The disease-image detection module 160 causes the computer to function as the disease-image determination section 28. The output module 170 causes the computer to function as the output section 30.

These module configurations are only simplified representations of one technique for programming the program 100, and it should be noted that programming techniques having similar functions as the program 100 are not limited to these module configurations.

Next, a neurodegenerative disorders image detection method according to the present invention will be described. FIG. 7 and FIG. 8 are flow charts showing processes in preferred modes of the neurodegenerative disorders detection method according to the present invention. As can be seen from these diagrams, the neurodegenerative disorders image detection method according to the present invention may be implemented by executing the neurodegenerative disorders image detection program described above. However, it is not always necessary to program this method, and the method may be implemented by providing instructions related to each step directly into the computer.

Several examples of preferred embodiments of the present invention have been described based on the drawings, but embodiments of the present invention are not limited to these examples and may take on various configurations without deviating from the sprit of the present invention. For example, in the above examples, the regions of interest used in significance tests were defined on brain functional images to which the anatomic standardization has not been applied. But as long as these regions can be defined on brain functional images derived from a subject, any techniques can be employed without any limitations. For example, it is possible to use a technique in which the operator defines the functionally deteriorated site and the functionally preserved site based on visual observation for each acquired brain functional image. Further, a technique may be used in which region-of-interest data defined on a standard brain are transformed to the form of a brain functional image of a subject using inverse transformation, and the transformed region-of-interest data are overlapped on the brain functional image of the subject to define regions of interest on the brain functional image of the subject.

Because the technique according to the present invention is a technique based on a significance test between a disease-specific functionally deteriorated site and functionally preserved site, it may also be applied for other neurodegenerative disorders by applying the functionally deteriorated sites and functionally preserved sites unique to various diseases to the brain functional images of a subject.

EXPLANATION OF THE SYMBOLS

Figure 1A:
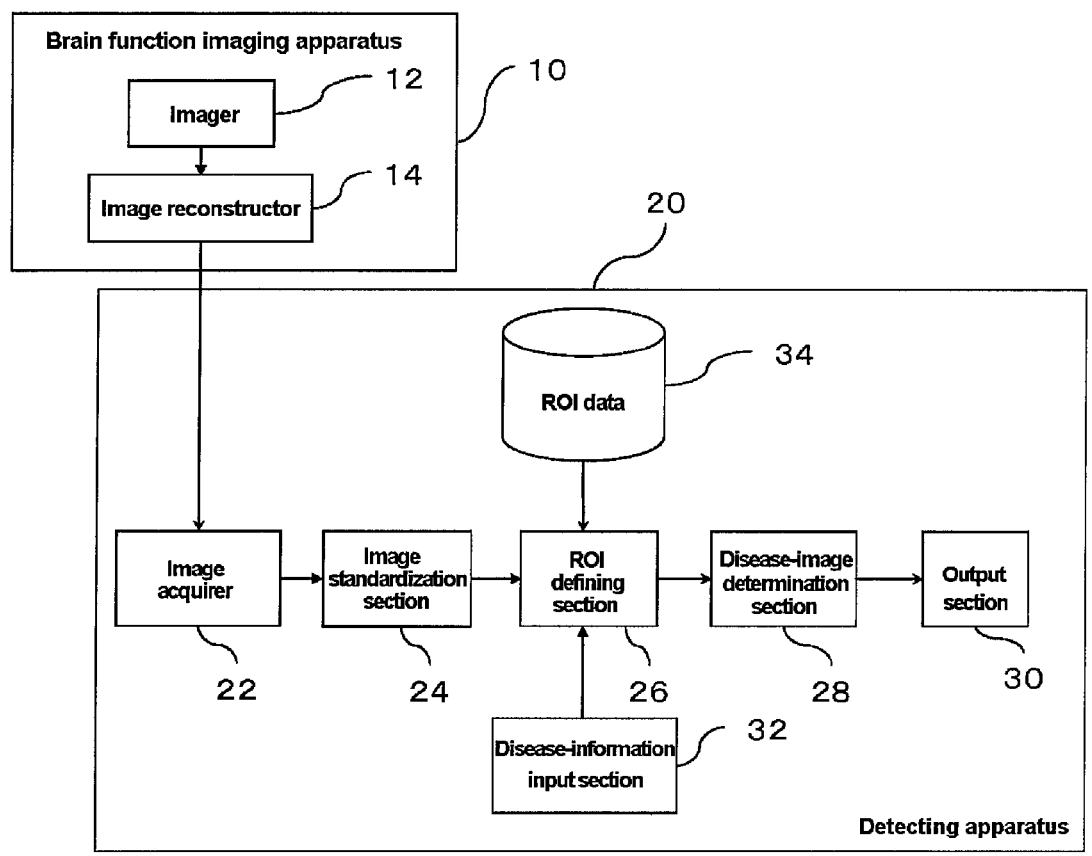
FIG. 1A is a diagram showing one example of the functional configuration of a neurodegenerative disorders image detecting apparatus according to the present invention.
Figure 1B:
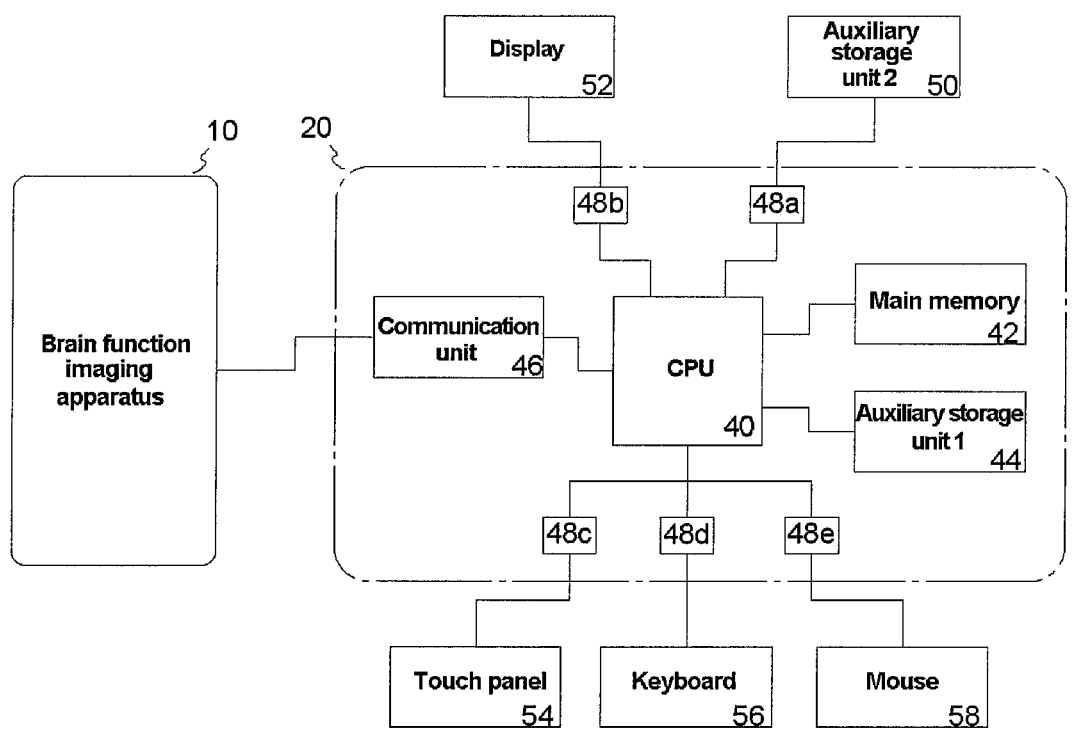
FIG. 1B is a diagram showing one example of the hardware configuration of a neurodegenerative disorders image detecting apparatus according to the present invention.
Figure 2:
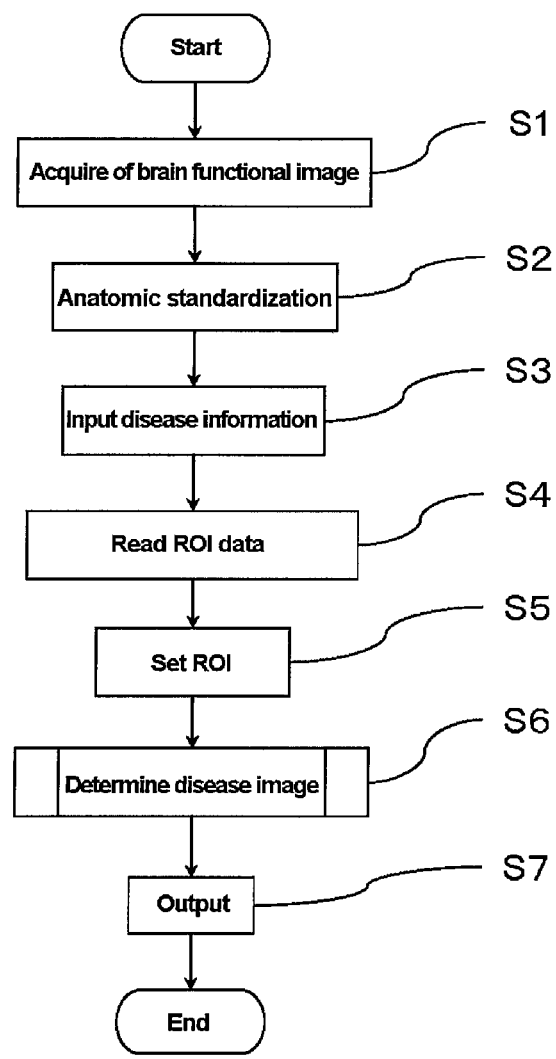
FIG. 2 is a diagram showing one example of the operations of a neurodegenerative disorders image detecting apparatus according to the present invention.
Figure 3:
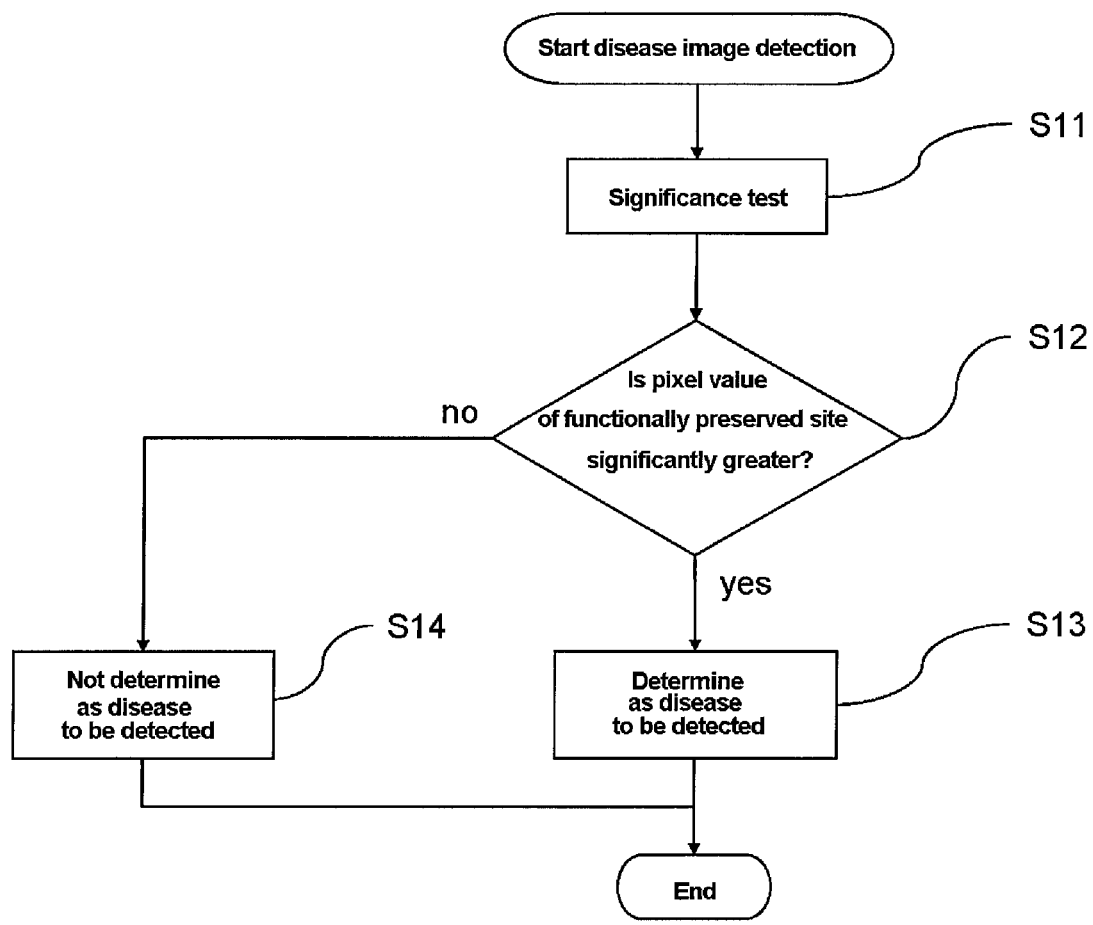
FIG. 3 is a diagram showing one example of the process flow of a disease-image detection process of a neurodegenerative disorders image detecting apparatus according to the present invention.
Figure 4:
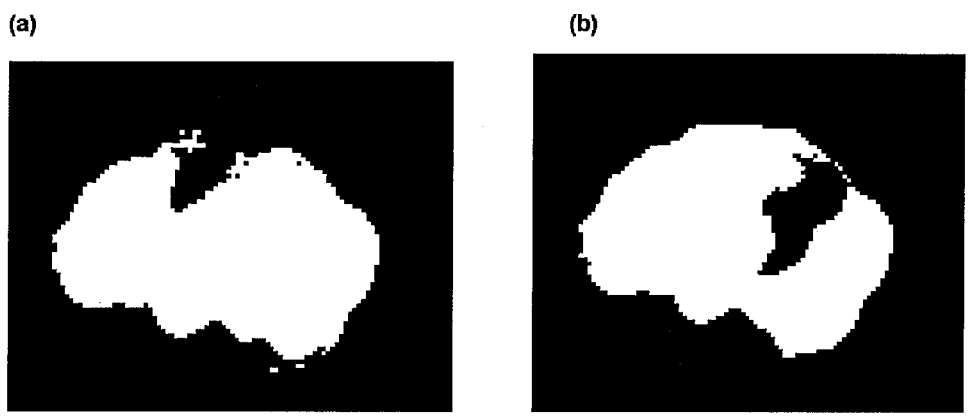
FIG. 4 is a diagram showing an example extraction of region-of-interest data based on the present technique, where (a) shows a functionally preserved part and (b) shows a functionally deteriorated part.
Figure 5:
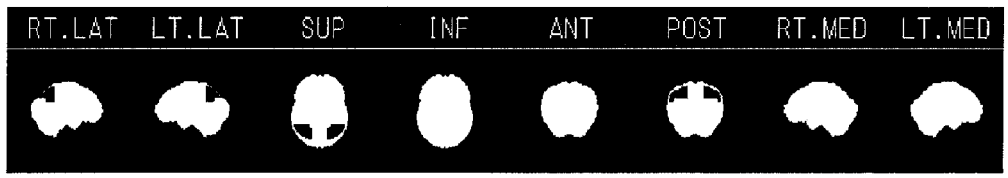
FIG. 5 is a diagram showing one example of a template, where (a) shows the parietal lobe, (b) shows the temporal lobe, (c) shows the sensorimotor area, (d) shows the frontal lobe, (e) shows the occipital lobe, (f) shows the posterior cingulate gyrus, and (g) shows the anterior cingulate gyrus.
Figure 5:
Figure 5:
Figure 5:
Figure 5:
Figure 5:
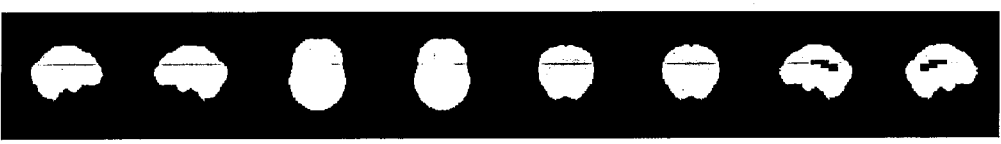
Figure 5:
Figure 6:
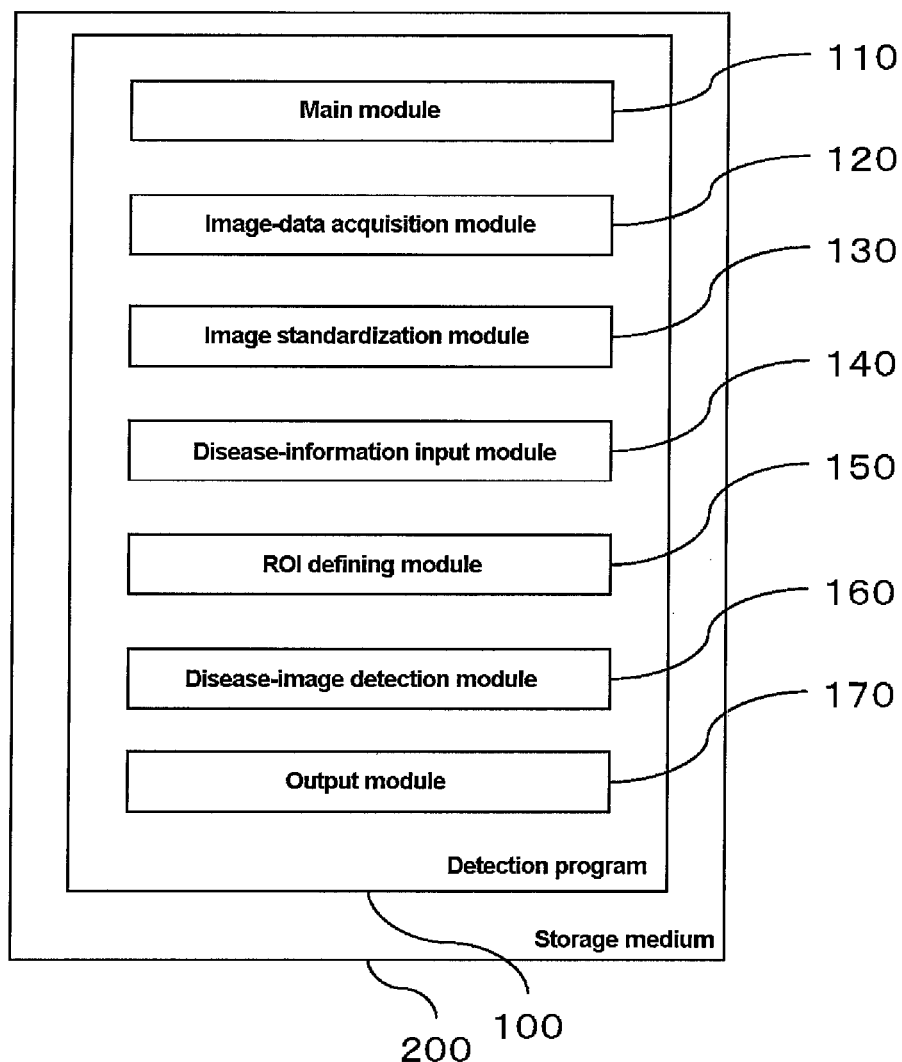
FIG. 6 is a diagram showing one example of the configuration of a neurodegenerative disorder image detection program according to the present invention.
Figure 7:
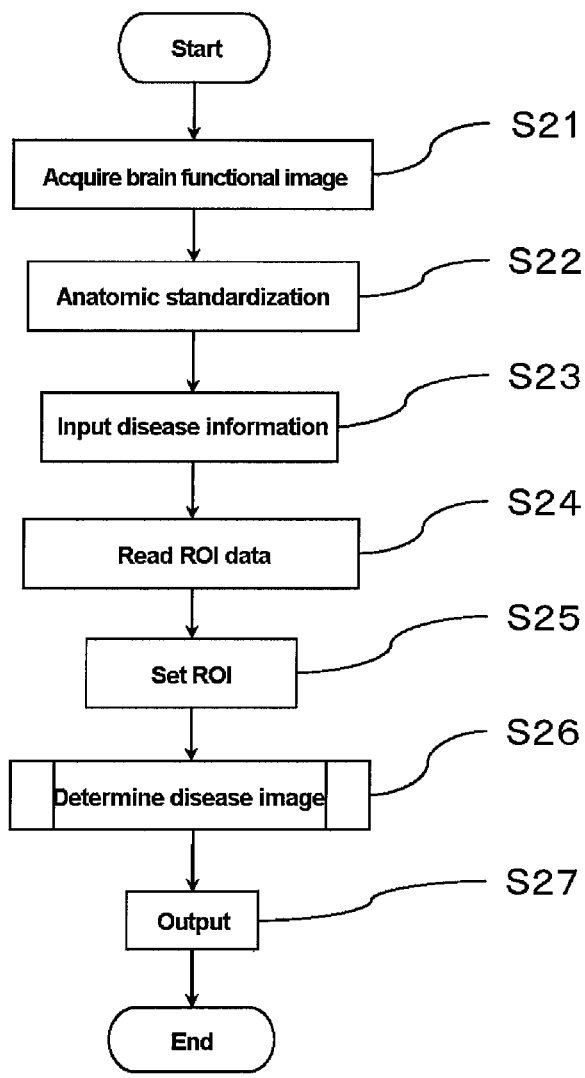
FIG. 7 is a flow chart showing the processes of one example of a neurodegenerative disorders image detection method according to the present invention.
Figure 8:
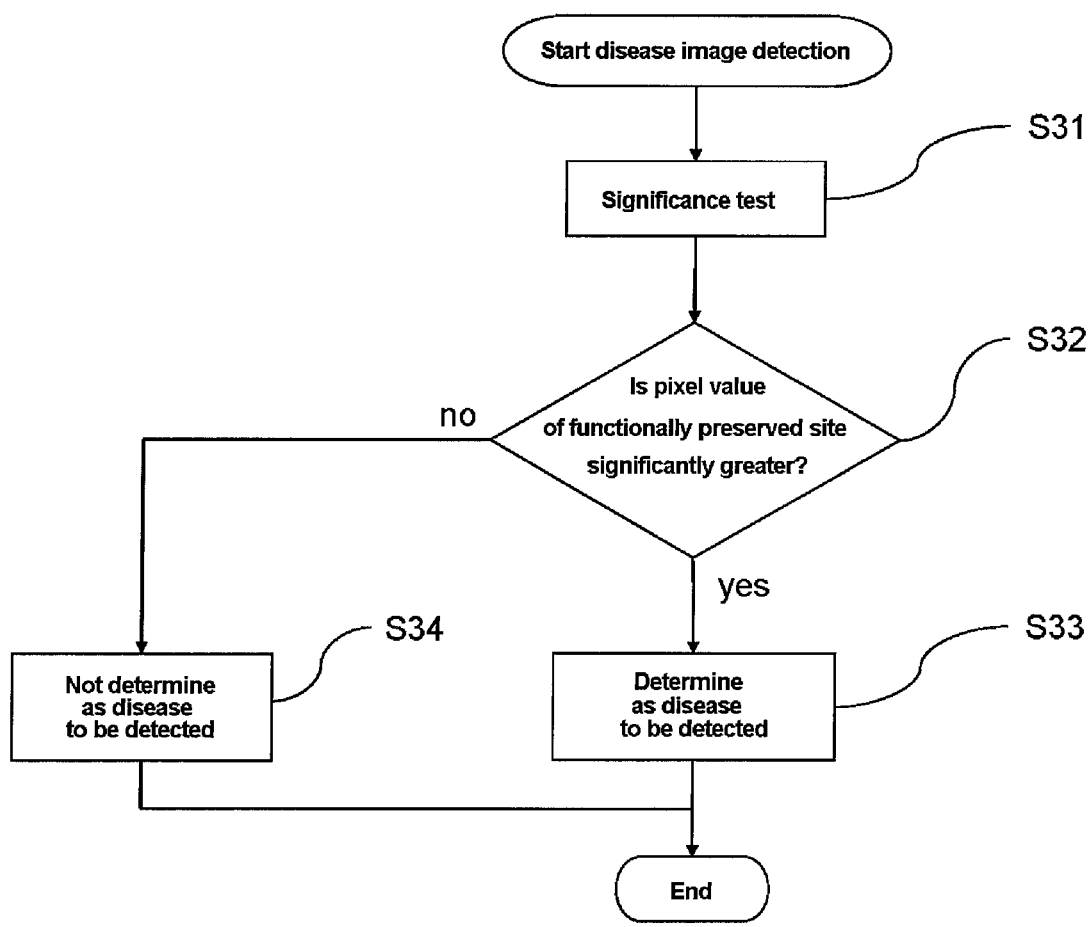
FIG. 8 is a flow chart showing the disease-image detection process of one example of a neurodegenerative disorders image detection method according to the present invention.
Figure 9:
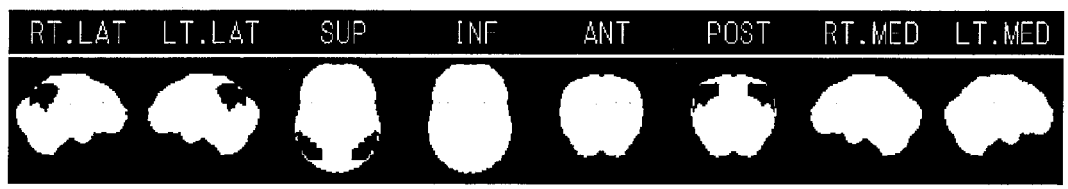
FIG. 9 shows the regions of interest defined in Demonstration 1, where (a) shows the functionally deteriorated part and (b) shows the functionally preserved part.
Figure 9:
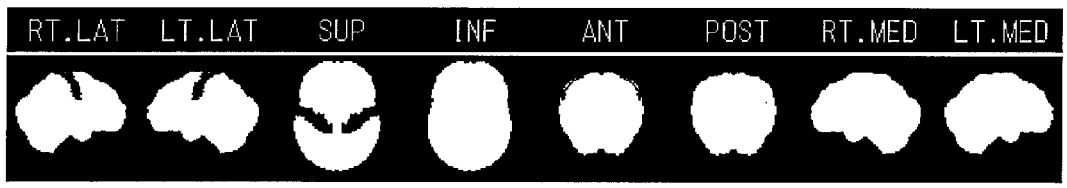

10: Brain function imaging apparatus
12: Imager
14: Image reconstructor
20: Neurodegenerative disorders image detecting apparatus
22: Image acquirer
24: Image standardization section
26: Region-of-interest defining section
28: Disease-image determination section
30: Output section
32: Disease-information input section
34: Region-of-interest data
100: Neurodegenerative disorders image detection program
110: Main module
120: Image-data acquisition module
130: Image standardization module
140: Disease-information input module
150: Region-of-interest defining module
160: Disease-image detection module
170: Output module
200: Storage medium

The invention claimed is:

1. A neurodegenerative disorders detecting apparatus that is capable of handling brain functional images, comprising:
   a processor; and
   a memory communicatively coupled to the processor when the apparatus is operational, the memory bearing instructions that, upon execution by the processor, cause the processor to perform operations comprising:
   defining, for a set of brain functional images for a subject, regions of interest in a functionally deteriorated site where functions could be specifically deteriorated in a neurodegenerative disorder to be detected, and a functionally preserved site where functions could be preserved even in said neurodegenerative disorder to be detected, respectively; and conducting a significance test using pixel values within the regions of interest defined for each of the functionally deteriorated site and the functionally preserved site, and determining that the neurodegenerative disorder to be detected exists when the mean pixel value of said regions of interest in the functionally preserved site is significantly greater than the mean pixel value of the regions of interest in the functionally deteriorated site.

2. The neurodegenerative disorders detecting apparatus of claim 1, wherein defining, for the set of brain functional images, regions of interest in a functionally deteriorated site comprises:

defining regions of interest in the functionally deteriorated site and the functionally preserved site, respectively, based on the region-of-interest data retrieved from a region-of-interest database based on disease information of the neurodegenerative disorder to be detected.

3. The neurodegenerative disorders detecting apparatus of claim 2, wherein, in response to the neurodegenerative disorder to be detected being Alzheimer's disease, a parietal lobe is defined as said functionally deteriorated site and a sensorimotor area is defined as said functionally preserved site.

4. The neurodegenerative disorders detecting apparatus of claim 1, wherein, in response to the neurodegenerative disorder to be detected being Lewy body dementia, an occipital lobe is defined as said functionally deteriorated site and a sensorimotor area is defined as said functionally preserved site.

5. The neurodegenerative disorders detecting apparatus of claim 1, wherein defining for the set of brain functional images, regions of interest in a functionally deteriorated site comprises:

applying anatomic standardization for the set of brain functional images; and defining regions of interest in the functionally deteriorated site and the functionally preserved site, respectively, on the set of brain functional images to which the anatomic standardization has been applied for the neurodegenerative disorder to be detected.

6. The neurodegenerative disorders detecting apparatus of claim 1, wherein defining for the set of brain functional images, regions of interest in a functionally deteriorated site comprises:

obtaining transformation parameters for anatomic standardization;

applying anatomic standardization for the set of brain functional images based on the transformation parameters;

matching the shape of the region-of-interest data with the brain shape of the set of brain functional images by transforming the region-of-interest data using the transformation parameters; and defining regions of interest in both the functionally deteriorated site and the functionally preserved site by applying the transformed region-of-interest data to the set of brain functional images to which the anatomic standardization has not been applied.

7. A non-transitory computer-readable storage medium bearing computer-executable instructions that, when executed upon a computer, cause the computer to perform operations comprising:

storing first image data corresponding to a first region of a set of brain functional images for a subject, wherein the image data corresponds to a functionally deteriorated site where functions could be specifically deteriorated in a neurodegenerative disorder to be detected;

storing second image data corresponding to a second region in the set of brain functional images, wherein the second image data corresponds to a functionally preserved site where functions could be preserved even in the neurodegenerative disorder to be detected; and determining neurodegenerative disorders based on a significance test between pixel values of the first image data and pixel values of the second image data.

8. The non-transitory computer-readable storage medium of claim 7, wherein determining neurodegenerative disorders based on a significance test between pixel values of the first image data and pixel values of the second image data comprises:

determining that the neurodegenerative disorder to be detected exists in response to determining that the mean pixel value of the second image data is significantly greater than the mean pixel value of the first image data.

9. The non-transitory computer-readable storage medium of claim 7, further bearing computer-readable instructions that, when executed upon the computer, cause the computer to perform operations comprising:

defining the first region and the second region in response to operator inputs made through a user interface of the computer.

10. The non-transitory computer-readable storage medium of claim 7, further bearing computer-readable instructions that, when executed upon the computer, cause the computer to perform operations comprising:

defining the first region and the second region based on region-of-interest data stored on the computer.

11. The non-transitory computer-readable storage medium of claim 10, further bearing computer-readable instructions that, when executed upon the computer, cause the computer to perform operations comprising:

defining the first region and the second region in accordance with a type of neurodegenerative disorders to be detected.

12. The non-transitory computer-readable storage medium of claim 11, wherein the neurodegenerative disorder to be detected is Alzheimer's disease, and wherein defining the first region and the second region based on region-of-interest data stored on the computer comprises:

defining a parietal lobe as the first region and a sensorimotor area as the second region.

13. The non-transitory computer-readable storage medium of claim 11, wherein the neurodegenerative disorder to be detected is Lewy body dementia, and wherein defining the first region and the second region based on region-of-interest data stored on the computer comprises:

defining an occipital lobe as the first region and a sensorimotor area as the second region.

14. The non-transitory computer-readable storage medium of claim 10 wherein the region-of-interest data is data prepared for an anatomically standardized brain, and wherein defining the first region and the second region based on region-of-interest data stored on the computer comprises:

applying anatomic standardization for the brain functional image; and defining the first region and the second region on the standardized brain functional image.

15. The non-transitory computer-readable storage medium of claim 10 wherein the region-of-interest data is data prepared for an anatomically standardized brain, and wherein defining the first region and the second region based on region-of-interest data stored on the computer comprises:

applying anatomic standardization for the brain functional image to obtain transformation parameters for the anatomic standardization;

transforming the region-of-interest data using the transformation parameters to match the brain shape of the brain functional image; and defining the first region and the second region for the brain functional image to which the anatomic standardization has not been applied based on the transformed region-of-interest data.

16. A method for detecting neurodegenerative disorders, comprising:

determining first image data corresponding to a first region of a set of brain functional images for a subject, wherein the image data corresponds to a functionally deteriorated site where functions could be specifically deteriorated in a neurodegenerative disorder to be detected;

determining second image data corresponding to a second region in the set of brain functional images, wherein the second image data corresponds to a functionally preserved site where functions could be preserved even in the neurodegenerative disorder to be detected; and storing in a computer memory an indication that the neurodegenerative disorder to be detected exists based on a significance test between pixel values of the first image data and pixel values of the second image data.

17. The method of claim 16, wherein storing in a computer memory an indication that the neurodegenerative disorder to be detected exists based on a significance test between pixel values of the first image data and pixel values of the second image data comprises:

determining that the neurodegenerative disorder to be detected exists in response to determining that the mean pixel value of the second image data is significantly greater than the mean pixel value of the first image data.

18. The method of claim 16, further comprising:

defining the first region and the second region in response to user input received through a user interface of the computer.

19. The method of claim 16, further comprising:

defining the first region and the second region based on region-of-interest data stored on the computer.

20. The method of claim 16, further comprising:

defining the first region and the second region in accordance with a type of neurodegenerative disorders to be detected.

* * * * *